United States Patent
Okuda et al.

(10) Patent No.: US 7,491,310 B2
(45) Date of Patent: Feb. 17, 2009

(54) CONCENTRATION MEASURING METHOD AND CONCENTRATION MEASURING APPARATUS

(75) Inventors: Hisashi Okuda, Kyoto (JP); Yoshimi Oura, Kyoto (JP); Kotaro Kado, Kyoto (JP)

(73) Assignee: Arkray, Inc., Kyoto (JP)

( * ) Notice: Subject to any disclaimer, the term of this patent is extended or adjusted under 35 U.S.C. 154(b) by 952 days.

(21) Appl. No.: 10/492,432

(22) PCT Filed: Oct. 9, 2002

(86) PCT No.: PCT/JP02/10505

§ 371 (c)(1),
(2), (4) Date: Apr. 12, 2004

(87) PCT Pub. No.: WO03/034055

PCT Pub. Date: Apr. 24, 2003

(65) Prior Publication Data

US 2004/0232009 A1 Nov. 25, 2004

(30) Foreign Application Priority Data

Oct. 12, 2001 (JP) .............................. 2001-315552
Oct. 12, 2001 (JP) .............................. 2001-315553

(51) Int. Cl.
*G01N 27/327* (2006.01)
(52) U.S. Cl. ............... 205/777.5; 205/775; 204/403.02; 204/400
(58) Field of Classification Search .................. 204/412, 204/403.01–403, 15, 400, 403; 205/775, 205/778, 777.5, 792
See application file for complete search history.

(56) References Cited

U.S. PATENT DOCUMENTS

| 5,320,732 | A | 6/1994 | Nankai et al. |
| 5,582,697 | A | 12/1996 | Ikeda et al. |
| 5,628,890 | A | 5/1997 | Carter et al. ................. 204/403 |
| 5,650,062 | A * | 7/1997 | Ikeda et al. .................. 205/778 |
| 6,377,896 | B1 | 4/2002 | Sato et al. |
| 7,312,087 | B2 * | 12/2007 | Duong et al. ............... 436/149 |

FOREIGN PATENT DOCUMENTS

EP      0546536 A1    10/1992

(Continued)

*Primary Examiner*—Alex Noguerola
(74) *Attorney, Agent, or Firm*—Hamre, Schumann, Mueller & Larson, P.C.

(57) ABSTRACT

The present invention relates to a technique for measuring the concentration of a particular component in a sample liquid using a test tool (2). The test tool (2) includes a first through a third detection elements (31a-33a) arranged in the mentioned order in the moving direction of the sample liquid for measuring an electro-physical quantity. The present invention provides a concentration measuring method which includes a first detection step for detecting whether or not liquid conduction is established between the first and the second detection elements (31a, 32a), a second detection step for detecting whether or not liquid conduction is established between the second and the third detection elements (31a, 33a), a measurement step for measuring an electro-physical quantity by using the first through the third detection elements (31a-33a), and a concentration computation step for computing the concentration of the particular component based on the electro-physical quantity. The present invention also provides a concentration measuring apparatus (1) for realizing the concentration measuring method.

6 Claims, 9 Drawing Sheets

FOREIGN PATENT DOCUMENTS

| | | |
|---|---|---|
| EP | 0 732 406 | 9/1996 |
| EP | 1 074 832 | 2/2001 |
| JP | 6-109688 | 4/1994 |
| JP | 8-10208 | 1/1996 |
| JP | 11-194108 | 7/1999 |
| JP | 2001-330581 | 11/2001 |

* cited by examiner

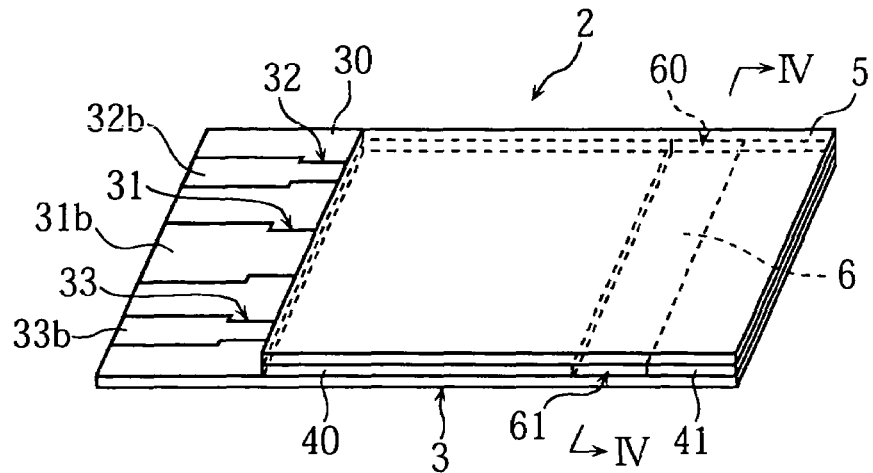
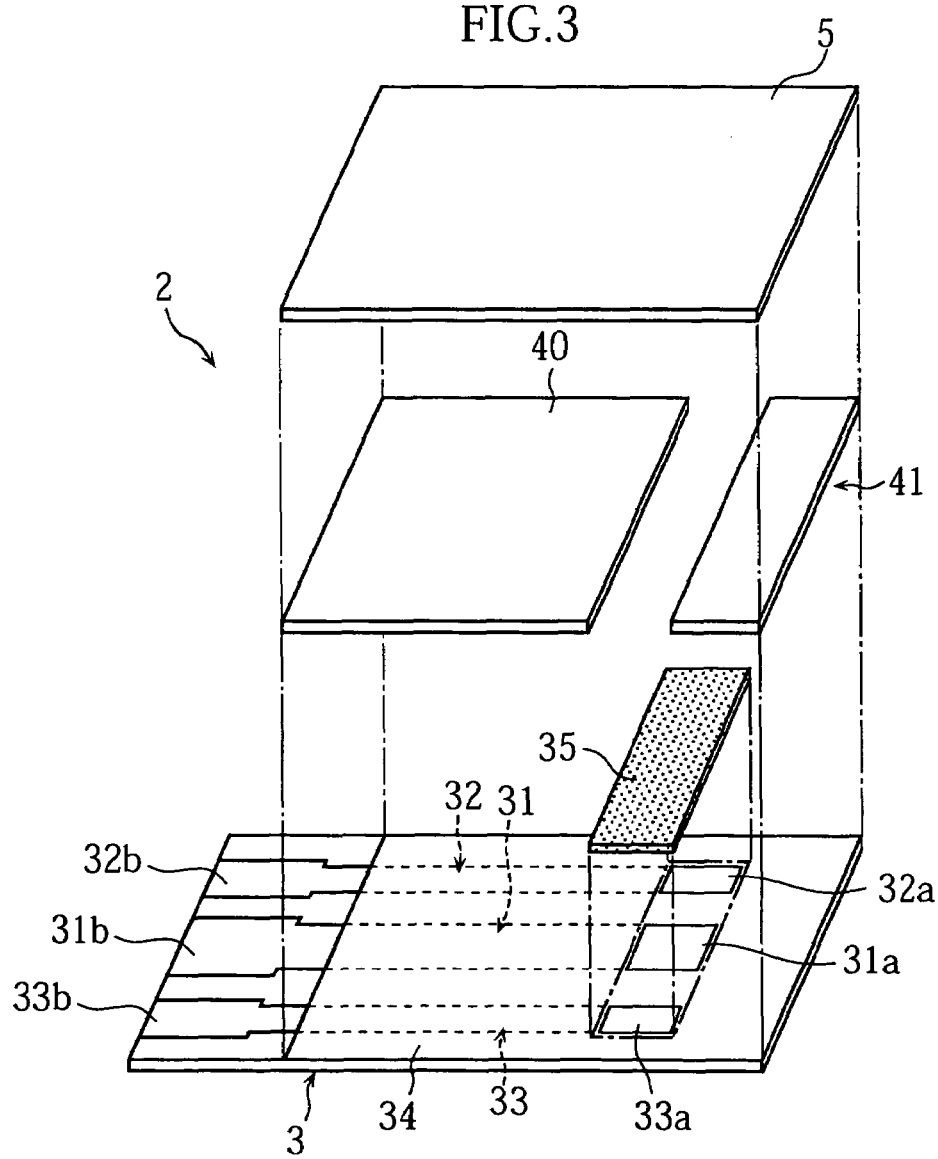

CONCENTRATION MEASURING METHOD AND CONCENTRATION MEASURING APPARATUS

This application is a 371 of PCT/JP02/10505, filed Oct. 09, 2002, which claims priority from Japanese application JP 2001-31552, field Oct. 12, 2001, and JP 2001-31553, filed Oct. 12, 2001.

TECHNICAL FIELD

The present invention relates to a technique for measuring the concentration of a particular component (e.g. glucose or cholesterol) contained in a sample liquid (e.g. blood or urine).

BACKGROUND ART

A popular method for measuring the concentration of a particular component contained in a sample liquid (e.g. glucose in blood) utilizes oxidation-reduction reaction. Portable hand-held blood glucose level measuring apparatuses are available so that the user can easily check the blood glucose level while staying at home or away from home. To measure the blood glucose level using such a portable blood glucose level measuring apparatus, a disposable biosensor for providing an enzyme reaction system is attached to the measuring apparatus, and then blood is supplied to biosensor for the measurement of the blood glucose level (See JP-B-8-10208, for example).

Various types of biosensors have been put to practical use, an example of which is shown in FIGS. 11 and 12 of the accompanying drawings. The illustrated biosensor 9 includes a substrate 92, a spacer 93, a cover 94, and a capillary 95 defined by these parts. The substrate 92 is formed with an operative electrode 90 and a counterpart electrode 91. A portion 90a of the operative electrode 90 and a portion 91a of the counterpart electrode 91 are located within the capillary 95 and connected to each other by a reagent portion 96. The reagent portion 96 contains oxidoreductase and an electron carrier. The cover 94 is formed with a discharge port 94a and laminated on the substrate 92 via the spacer 93. The interior of the capillary 95 communicates with the outside through an open end 93a of a slit 93A and the discharge port 94a.

For measuring the blood glucose level, blood is introduced to the capillary 95 of the biosensor 9, which is pre-mounted to the blood glucose level measuring apparatus. The blood moves through the capillary 95 to the discharge port 94a by capillary action while dissolving the reagent portion 96 to form a liquid phase reaction system in the capillary 95. The concentration measuring apparatus determines whether or not the sample liquid introduced into the capillary 95 based on to the response current (or the voltage converted from the response current) obtained by utilizing the operative electrode 90 and the counterpart electrode 91. Specifically, when the response current (or the responsive voltage) is equal to or higher than a predetermined threshold value, it is determined that the blood is supplied.

In the liquid phase reaction system in the capillary 95, the glucose in the blood is oxidized while the electron carrier is reduced by the catalytic reaction of oxidoreductase. When certain voltage is applied to the liquid phase reaction system, the electron carrier is oxidized (releases electrons), and the electrons released by the electron carrier is supplied to the operative electrode 90. The blood glucose level measuring apparatus measures the supply of electrons to the operative electrode 90 as the oxidation current, and computes the glucose level based on the oxidation current.

The response current reflects the supply of electrons to the operative electrode 90, and the electron supply to the operative electrode 90 reflects the amount of oxidized glucose, i.e. the glucose level. However, the blood contains blood cell components such as red blood cells, and the response current varies depending on the amount of the blood cell components. The amount of blood cell components in blood (hematocrit) differs among individuals and varies depending on physical condition even in the same person. Therefore, due to the influence of hematocrit, proper measurement may be impossible even when the same person performs measurement, let alone when the users are different. Further, the response current measured may be influenced not only by hematocrit but also by the degree of chyle or hemolysis of blood, for example.

The influence of hematocrit may be eliminated by a method in which the hematocrit of the blood is measured in advance and the blood glucose level is calculated while taking the hematocrit into consideration (See JP-A-11-194108, for example).

However, the concentration measurement by such a method is troublesome, because the hematocrit need be inputted in the blood glucose level measuring apparatus. The operation for inputting hematocrit is particularly troublesome in a medical facility, for example, in which a single blood glucose level measuring apparatus need be used frequently for measuring the blood glucose level of a large number of patients. Moreover, before the use of the blood glucose level measuring apparatus, another apparatus need be used for measuring the hematocrit of the patient, which makes the method further troublesome.

DISCLOSURE OF THE INVENTION

An object of the present invention is to make it possible to perform proper concentration measurement while taking the influence of another component contained in the sample liquid into consideration and avoiding posing a burden on the user.

According to a first aspect of the present invention, there is provided a concentration measuring method for measuring concentration of a particular component in a sample liquid using a test tool which comprises a capillary for moving the sample liquid, and a first through third detection elements for measuring an electro-physical quantity. The first through the third detection elements are arranged in the mentioned order from an upstream side toward a downstream side in the moving direction of the sample liquid. The method comprises a first detection step for detecting whether or not liquid conduction is established between the first detection element and the second detection element, a second detection step for detecting whether or not liquid conduction is established between the second detection element and the third detection element, a measurement step for measuring an electro-physical quantity for computation by using at least two of the first through the third detection elements, and a concentration computation step for computing the concentration of the particular component based on the electro-physical quantity for computation.

Examples of electro-physical quantity include current, voltage and resistance.

Preferably, the concentration measuring method of the present invention further comprises a time computation step for computing time taken from the detection of liquid conduction in the first detection step to the detection of liquid conduction in the second conduction step. In this case, the concentration computation step preferably comprises computing the concentration of the particular component while taking the computed time into consideration.

The concentration computation step may include data processing operation for correcting, based on a correction value, an electro-physical quantity for computation or a computed value obtained based on the electro-physical quantity for computation.

The computed value may be a voltage converted from a response current measured as the electro-physical quantity, or the concentration obtained by computation without correction. The correction value may be obtained by computation based on data showing a relationship between the time taken and a correction value.

Preferably, the second detection step comprises measuring an electro-physical quantity by using all of the first through the third detection elements and determining whether or not liquid conduction is established between the second detection element and the third detection element based on a time history of the electro-physical quantity.

Specifically, for example, the second detection step comprises measuring an electro-physical quantity at a plurality of predetermined measurement time points, computing a variation in current per unit time at each of the measurement time points, and determining that liquid conduction is established between the second detection element and the third detection element when the variation in current is greater than a predetermined threshold value.

The second detection step may comprise computing a difference between an electro-physical quantity measured at a certain measurement time point and an electro-physical quantity measured at another measurement time point directly before said certain measurement time point and determining that liquid conduction is established between the second detection element and the third detection element when the difference is greater than a predetermined threshold value.

Preferably, the third detection element is larger in surface area than the first detection element in the test tool.

Preferably, the concentration computation step comprises computing the concentration of the particular component based on a difference between an electro-physical quantity measured after a predetermined time has elapsed since liquid conduction between the second detection element and the third detection element was detected in the second detection step and another electro-physical quantity measured when liquid conduction between the second detection element and the third detection element is detected in the second step.

For example, the sample liquid may contain a coexisting component which causes an error in the concentration measurement of the particular component. In this case, the time taken is figured out as a reflection of influence of the coexisting component. When the sample liquid is blood, the coexisting component which causes a measurement error may be blood cells, and the particular component may be glucose. The sample liquid may be other biochemical samples such as urine or saliva, or samples other than biochemical samples.

According to a second aspect of the present invention, there is provided a concentration measuring apparatus for measuring concentration of a particular component in a sample liquid using a test tool which comprises a capillary for moving the sample liquid, and a first through a third detection elements for measuring an electro-physical quantity. The first through the third detection elements are arranged in the mentioned order from an upstream side toward a downstream side in the moving direction of the sample liquid. The apparatus comprises a detector for detecting whether or not liquid conduction is established between the first detection element and the second detection element as well as between the second detection element and the third detection element, an electro-physical quantity measurer for measuring an electro-physical quantity for computation by using at least two of the first through the third detection elements, and a computation unit for computing the concentration of the particular component based on the electro-physical quantity for computation.

Preferably, the concentration measuring apparatus further comprises a voltage application unit for applying a voltage across at least two detection elements selected from the first through the third detection elements. In this case, the electro-physical quantity measurer measures a current as the electro-physical quantity when the voltage application means applies the voltage. Alternatively, the electro-physical quantity measurer may measure e.g. resistance as the electro-physical quantity.

Preferably, the computation unit computes the time taken from the establishment of liquid conduction between the first detection element and the second detection element to the establishment of liquid conduction between the second detection element and the third detection element and computes the concentration of the particular component while taking the computed time into consideration.

For example, the electro-physical quantity measurer measures an electro-physical quantity at a plurality of measurement time points with predetermined intervals. Preferably, in this case, the detector determines whether or not liquid conduction is established between the second detection element and the third detection element based on a time-course of the electro-physical quantity.

Specifically, for example, the detector computes a variation in current per unit time at each of the measurement time points and determines that liquid conduction is established between the second detection element and the third detection element when the variation in current is greater than a predetermined threshold value. In the second detection step, the detector may compute a difference between an electro-physical quantity measured at a certain measurement time point and an electro-physical quantity measured at another measurement time point directly before said certain measurement time point and determine that liquid conduction is established between the second detection element and the third detection element when the difference is greater than a predetermined threshold value.

For example, the computation unit may compute the concentration of the particular component based on a difference between an electro-physical quantity measured after a predetermined time has elapsed since liquid conduction between the second detection element and the third detection element was detected by the detector and another electro-physical quantity measured when liquid conduction between the second detection element and the third detection element is detected by the detector.

BRIEF DESCRIPTION OF THE DRAWINGS

FIG. 2 is a perspective view of the biosensor shown in FIG. 1.

FIG. 3 is an exploded perspective view of the biosensor shown in FIG. 2.

BEST MODE FOR CARRYING OUT THE INVENTION

Preferred embodiments of the present invention will be described below with reference to the accompanying drawings.

FIGS. 1-5 illustrate a first embodiment of the present invention.

Figure 1:
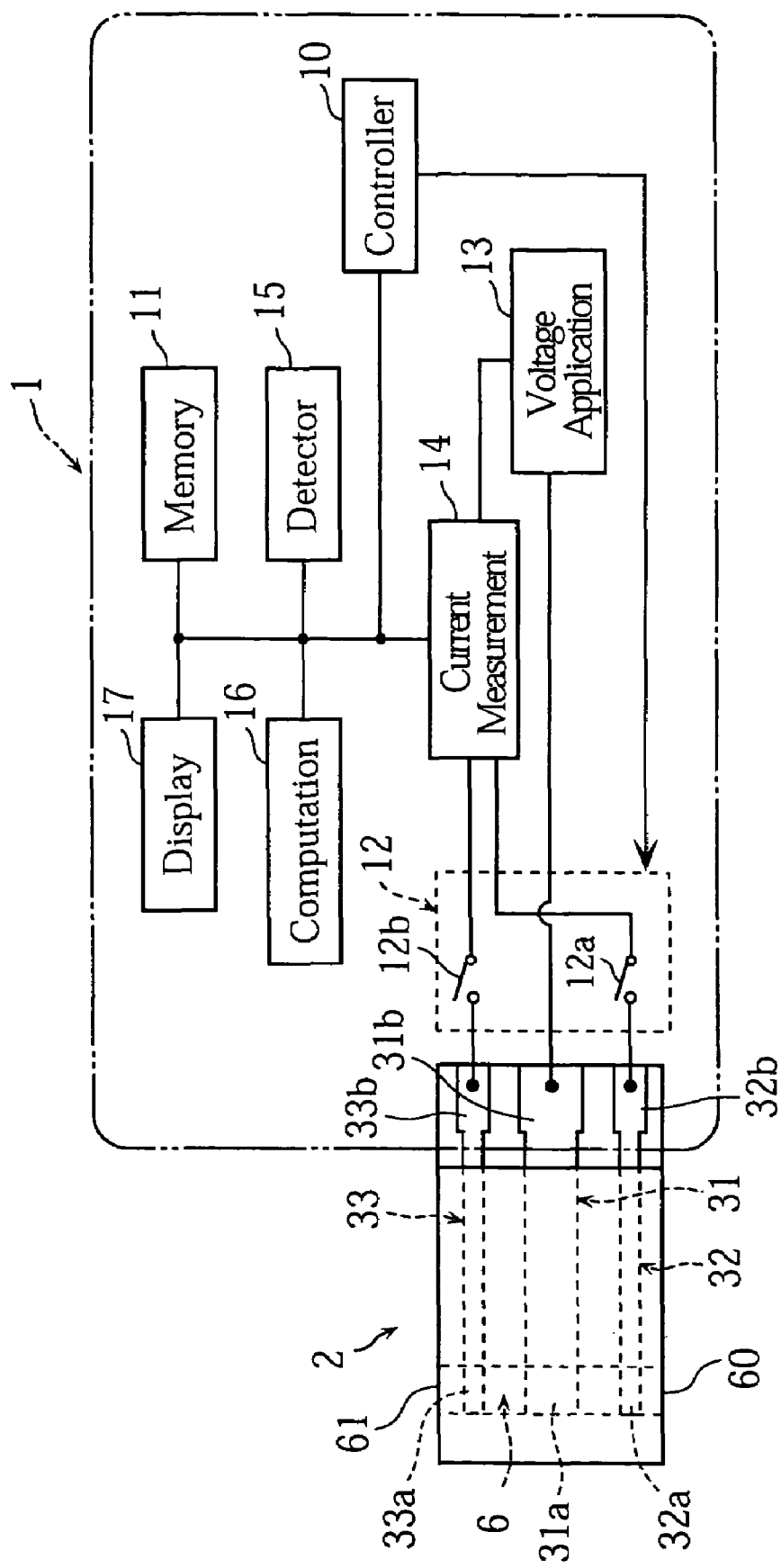
FIG. 1 is a view for describing a first embodiment of the present invention and schematically illustrates a concentration measuring apparatus to which a biosensor is attached.

As shown in FIG. 1, a concentration measuring apparatus 1 for measuring the concentration of a particular component in a sample liquid using a biosensor 2 includes a controller 10, a memory 11, a switching unit 12, a voltage application unit 13, a current measurer 14, a detector 15, a computation unit 16 and a display 17.

As shown in FIGS. 2 and 3, the biosensor 2 includes a substrate 3, a first and a second spacers 40, 41, a cover 5, and a capillary 6 defined by these parts.

The substrate 3 has an upper surface 30 formed with an operative electrode 31, a first counterpart electrode 32 and a second counterpart electrode 33 which extend longitudinally of the substrate 3. The electrodes 31-33 are spaced from each other widthwise of the substrate 3 and covered with an insulating film 34 except for pairs of opposite ends 31a-33a and 31b-33b. The ends 31a-33a of the operative electrode 31, first counterpart electrode 32 and second counterpart electrode 33 are connected to each other via a reagent portion 35. The reagent portion 35 is in a solid state and contains oxidoreductase and an electron carrier. The kind of oxidoreductase and electron carrier is selected depending on the kind of the component to be measured. To measure e.g. the glucose level, glucose dehydrogenase or glucose oxidase may be used as oxidoreductase, and potassium ferricyanide may be used as electron carrier, for example.

The cover 5 is laminated on the substrate 3 via the first and the second spacers 40 and 41. Each of the first and the second spacers 40 and 41, which are spaced from each other longitudinally of the substrate 3, has a predetermined thickness and extends widthwise of the substrate 3 to partially cover the substrate 3. Thus, the first and the second spacers 40, 41 define the thickness, width, and internal configuration of the capillary 6. Specifically, the capillary 6 has an internal space extending widthwise of the substrate 3 and communicating with the outside through openings 60, 61.

Figure 4A:
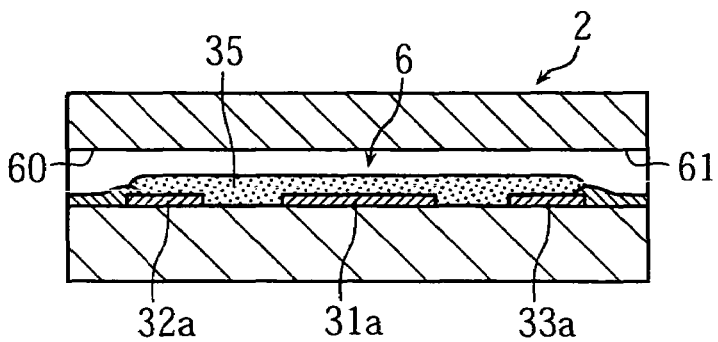
FIGS. 4A-4E are sectional views taken along lines IV-IV in FIG. 2 for describing the movement of the blood in the capillary.
Figure 4B:
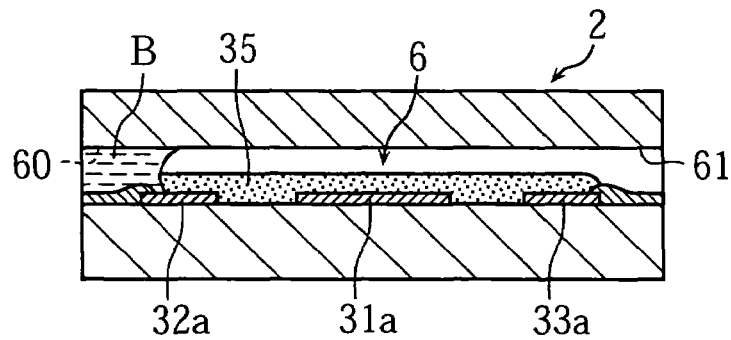
Figure 4C:
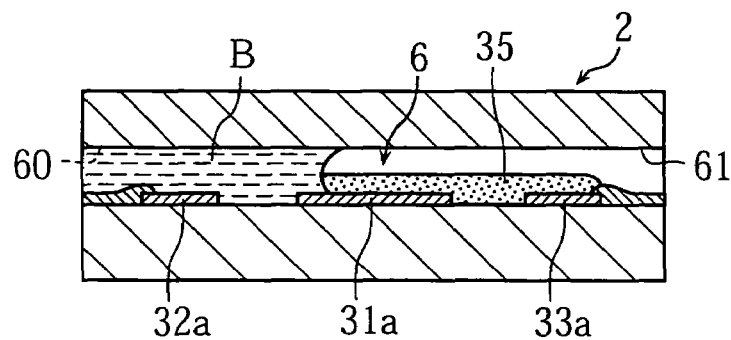
Figure 4D:
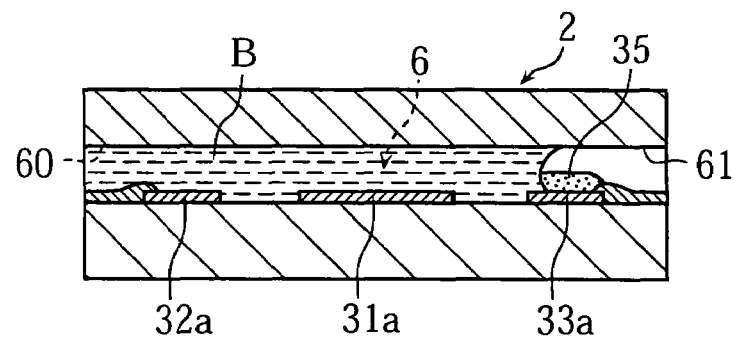
Figure 4E:
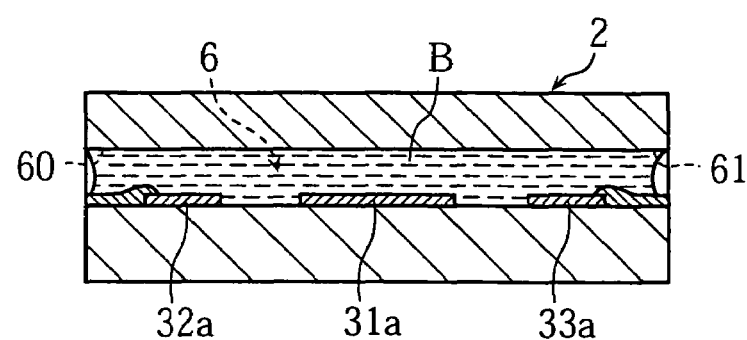

In the biosensor 2, when a sample liquid B is introduced through the opening 60, the sample liquid moves through the capillary 6 toward the opening 61 by capillary action, as shown in FIGS. 4A-4D, and eventually fills the internal space of the capillary 6, as shown in FIG. 4E. During the movement, the sample liquid B dissolves the reagent portion 35 to form a liquid phase reaction system in the capillary 6. In the liquid phase reaction system, oxidation-reduction reaction occurs to produce a reaction product in accordance with the amount of the component to be measured. In measuring glucose level, glucose is oxidized, while the electron carrier is reduced. When a voltage is applied to the liquid phase reaction system by utilizing the operative electrode 31 and at least one of the counterpart electrodes 32 and 33, for example, the reduced electron carrier releases the electrons. The electrons released from the electron carrier are supplied to the operative electrode 31.

The controller 10 shown in FIG. 1 controls the operation of each of the units 12-17.

The memory 11 stores programs and data necessary for operating the units 12-17. For instance, the data stored in the memory 11 may include that as to a calibration curve showing the relationship between a response current (or the voltage converted from the current) and the glucose level, and that as to correction values used for computing the concentration in the computation unit 16. For instance, the data as to correction values is stored in the form of a table or a formula as associated with the time taken from when liquid conduction is established between the end 31a of the operative electrode 31 and the 32a of the first counterpart electrode 32 till when liquid conduction is established between the end 31a of the operative electrode 31 and the 33a of the second counterpart electrode 33.

The switching unit 12 includes a first switch 12a and a second switch 12b. The switches 12a and 12b are turned on and off individually by the controller 10. By individually turning on or off the first switch 12a and the second switch 12b, the voltage application unit 13 and the current measurer 14 are electrically connected to selected one or both of the first counterpart electrode 32 and the second counterpart electrode 33.

The voltage application unit 13 serves to apply a voltage across the operative electrode 31 and the counterpart electrodes 32, 33. The voltage application unit 13 includes a DC power source such as a dry cell or a rechargeable battery.

The current measurer 14 measures the response current when a voltage is applied across the operative electrode 31 and at least one of the counterpart electrodes 32, 33.

The detector 15 detects whether or not liquid conduction is established between the ends 31a of the operative electrode 31 and the end 32a of the first counterpart electrode 32 or between the ends 31a of the operative electrode 31 and the end 33a of the second counterpart electrode 33 when the sample liquid is introduced into the capillary 6.

The computation unit 16 computes the time taken from the occurrence of liquid conduction between the end 31a of the operative electrode 31 and the end 32a of the first counterpart electrode 32 to the occurrence of liquid conduction between the end 31a of the operative electrode 31 and the end 33a of the second counterpart electrode 33. Based on the computed time, the computation unit computes the correction value necessary for the computation of the concentration of the particular component in the sample liquid. The computation unit computes the concentration based on the correction value and the current measured by the current measurer 14.

The display 17 is provided for displaying measurement results or an error message, for example. The display 17 may comprise a liquid crystal display, for example.

Each of the controller 10, the memory 11, the detector 15 and the computation unit 16 may comprise one of a CPU, a ROM and a RAM or a combination of these components. Alternatively, all of the units 10, 11, 15 and 16 may be provided by connecting a plurality of memories to a single CPU.

Figure 5:
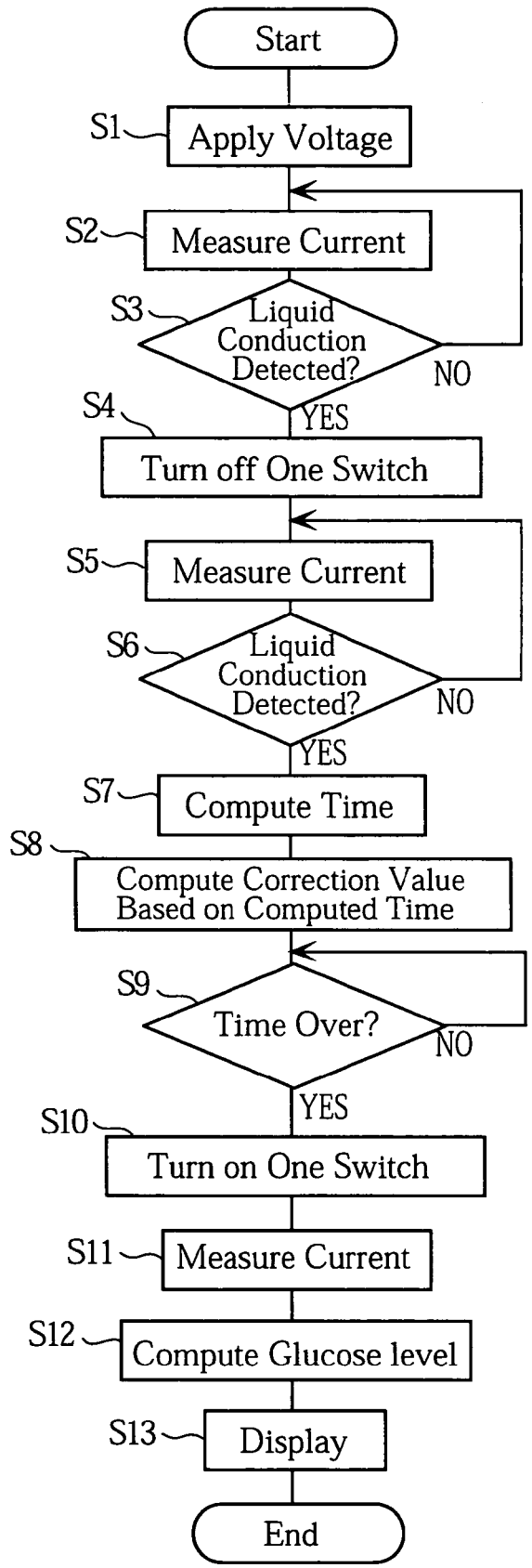
FIG. 5 is a flowchart for describing the concentration measurement operation.

The method for measuring the blood glucose level using the concentration measuring apparatus 1 and biosensor 2 will be described below with reference to FIGS. 1-4 and the flowchart shown in FIG. 5. Herein, it is assumed that the first and the second switches 11*a* and 11*b* are on before the biosensor 2 is mounted to the concentration measuring apparatus 1.

First, for measuring the blood glucose level, the biosensor 2 is mounted to the concentration measuring apparatus 1, and blood is introduced into the capillary 6 of the biosensor 2 through the opening 60 or the opening 61.

In the concentration measuring apparatus 1, the voltage application unit 13 applies a voltage across the operative electrode 31 and the first counterpart electrode 32 and across the operative electrode 31 and the second counterpart electrode 33 of the biosensor 2 (S1). The current measurer 14 measures the response current (S2).

The detector 15 checks whether or not liquid conduction is established between the end 31*a* of the operative electrode 31 and the end 32*a* of the first counterpart electrode 32 or between the end 31*a* of the operative electrode 31 and the end 33*a* of the second counterpart electrode 33 (S3). Specifically, the detector 15 monitors the response current measured by the current measurer 14 and checks whether or not the response current exceeds a predetermined threshold value. When the response current exceeds the threshold value, the detector 15 determines that the interior of the capillary is in the state as shown in FIG. 4C, for example, and that liquid conduction is established (S3: YES). When the response current does not exceed the threshold value, the detector 15 determines that the interior of the capillary is in the state as shown in FIG. 4A or 4B, for example, and that liquid conduction is not provided (S3: NO).

When the detector 15 does not detect the liquid conduction (S3: NO), the current measurement in S2 and the check in S3 are repetitively performed until the detector 15 detects the liquid conduction (S3: YES). In this case, the measurement of the response current in S2 is performed every 0.05 to 0.2 seconds, for example. When the liquid conduction is not detected even when the check is performed more than a predetermined number of times or even after a predetermined time has elapsed, the operation may be treated as an error.

When the liquid conduction is detected by the detector 15 (S3: YES), It is determined that the blood has entered the capillary 6, and the controller 10 turns off one of the first switch 12*a* and the second switch 12*b* (S4). For instance, when the liquid conduction between the end 31*a* of the operative electrode 31 and the end 32*a* of the first counterpart electrode 32 is detected, it is determined that the blood introduction into the capillary 6 is performed through the opening 61. In this case, the controller turns off the first switch 12*a*. In this state, voltage application and current measurement using the operative electrode 31 and the second counterpart electrode 33 is possible. On the other hand, when the liquid conduction between the end 31*a* of the operative electrode 31 and the end 33*a* of the second counterpart electrode 33 is detected, it is determined that the blood introduction into the capillary 6 is performed through the opening 60. In this case, the controller turns off the second switch 12*b*. In this state, voltage application and current measurement using the operative electrode 31 and the first counterpart electrode 32 is possible.

After one of the switches 12*a* and 12*b* is turned off, the current measurer 14 measures the response current (S5), and the detector 15 checks the liquid conduction again (S6). Specifically, in the case where the liquid conduction between the end 31*a* of the operative electrode 31 and the end 32*a* of the first counterpart electrode 32 is detected in S3, the detector checks, in S6, whether or not liquid conduction is established between the end 31*a* of the operative electrode 31 and the end 33*a* of the second counterpart electrode 33. On the other hand, in the case where the liquid conduction between the end 31*a* of the operative electrode 31 and the end 33*a* of the second counterpart electrode 33 is detected in S3, the detector checks, in S6, whether or not liquid conduction is established between the end 31*a* of the operative electrode 31 and the end 32*a* of the first counterpart electrode 32. The determination of whether or not the liquid conduction is established and the process when the liquid conduction is not detected (S6: NO) are performed similarly to S3.

When the liquid conduction is detected in S6 (S6:YES), the computation unit 16 computes the time taken from the detection of the liquid conduction in S3 (See FIG. 4C) to the detection of the liquid conduction in S6 (See FIG. 4D) (S7), and computes the correction value based on the computed time (S8). The correction value is computed based on a lookup table stored in the memory 11 and showing the relationship between the time taken and correction values. The correction value may be one for correcting the response current (or the voltage converted from the current) or one for correcting the value obtained by computation using a calibration curve.

In the detector 15, it is checked whether or not a predetermined time has elapsed since the liquid conduction was detected in S6 (S9). This check is repetitively performed until the detector 15 determines that the predetermined time has elapsed (S9: YES). When the detector 15 determines that the predetermined time has elapsed (S9: YES), the controller 10 turns on the switch 12*a* (or 12*b*) which has turned off in S4, and the current measurer 14 measures the response current for the concentration computation (S11). It is to be noted that the switch 12*a* (or 12*b*) which has turned off in S4 need not necessarily be turned on in the current measurement in S11. The measurement of response current may be performed at predetermined intervals after the liquid conduction is detected in S6. In this case, the response current at a certain time after the detection of liquid conduction in S6 may be sampled and used as the response current for the computation. The measurement of the response current for the computation in S11 may be performed after a predetermined time has elapsed since the electrical conduction was detected in S3.

Subsequently, the computation unit 16 computes the blood glucose level based on the response current for the computation and the correction value (S12). The computation of the blood glucose level is performed by using a calibration curve showing the relationship between the response current (or the voltage converted from the current) and the blood glucose level, for example. The computation result is displayed at the display 17 (S13).

When whole blood is used as the sample liquid, the sample liquid contains blood cell components in addition to the component to be measured. The proportion of blood cell components in the blood, which is represented as hematocrit, influences the measurement result. As the hematocrit increases, the viscosity of the blood increases, whereby the travel speed of the blood through the capillary 6 decreases. Therefore, when the blood glucose level is computed taking the travel speed of the blood through the capillary into consideration, a proper value which compensates for the influence of hematocrit can be obtained.

In this embodiment, the travel speed of the blood is found out in the concentration measuring apparatus 1 by measuring the time taken from the occurrence of liquid conduction between the end 31*a* of the operative electrode 31 and the end 32*a* of the first counterpart electrode 32 to the occurrence of liquid conduction between the end 31a of the operative electrode 31 and the end 33a of the second counterpart electrode 33, for example. Therefore, it is not necessary to measure the hematocrit value in advance or to input the hematocrit value into the concentration measuring apparatus 1. Therefore, it is possible to obtain a proper measurement result which compensates for the influence of hematocrit while reducing the burden posed on the measurer or user in performing the measurement.

FIGS. 6-10 illustrate a second embodiment of the present invention. In these figures, parts or elements which are identical or similar to those of the foregoing embodiment are designated by the same reference signs as those used for the foregoing embodiment, and detailed description thereof will be omitted.

Figure 7:
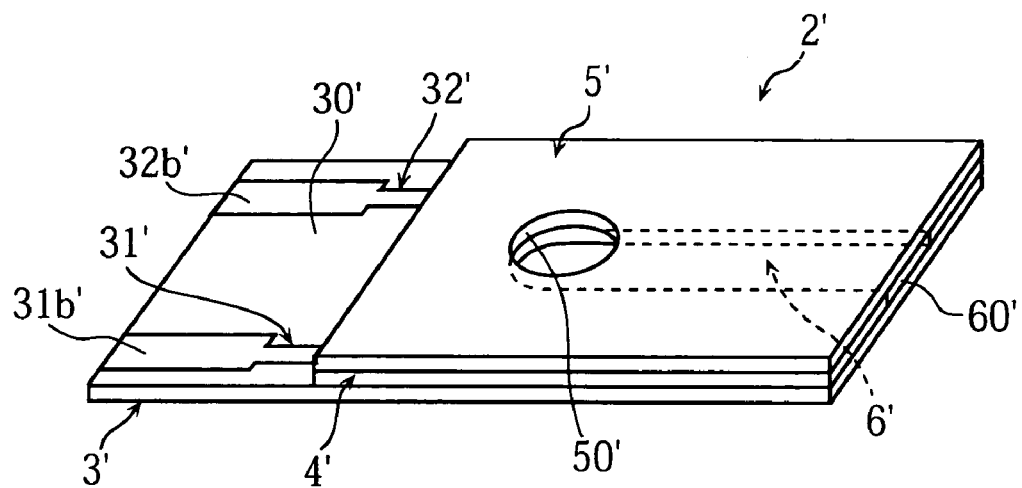
FIG. 7 is a perspective view of the biosensor shown in FIG. 6.
Figure 8:
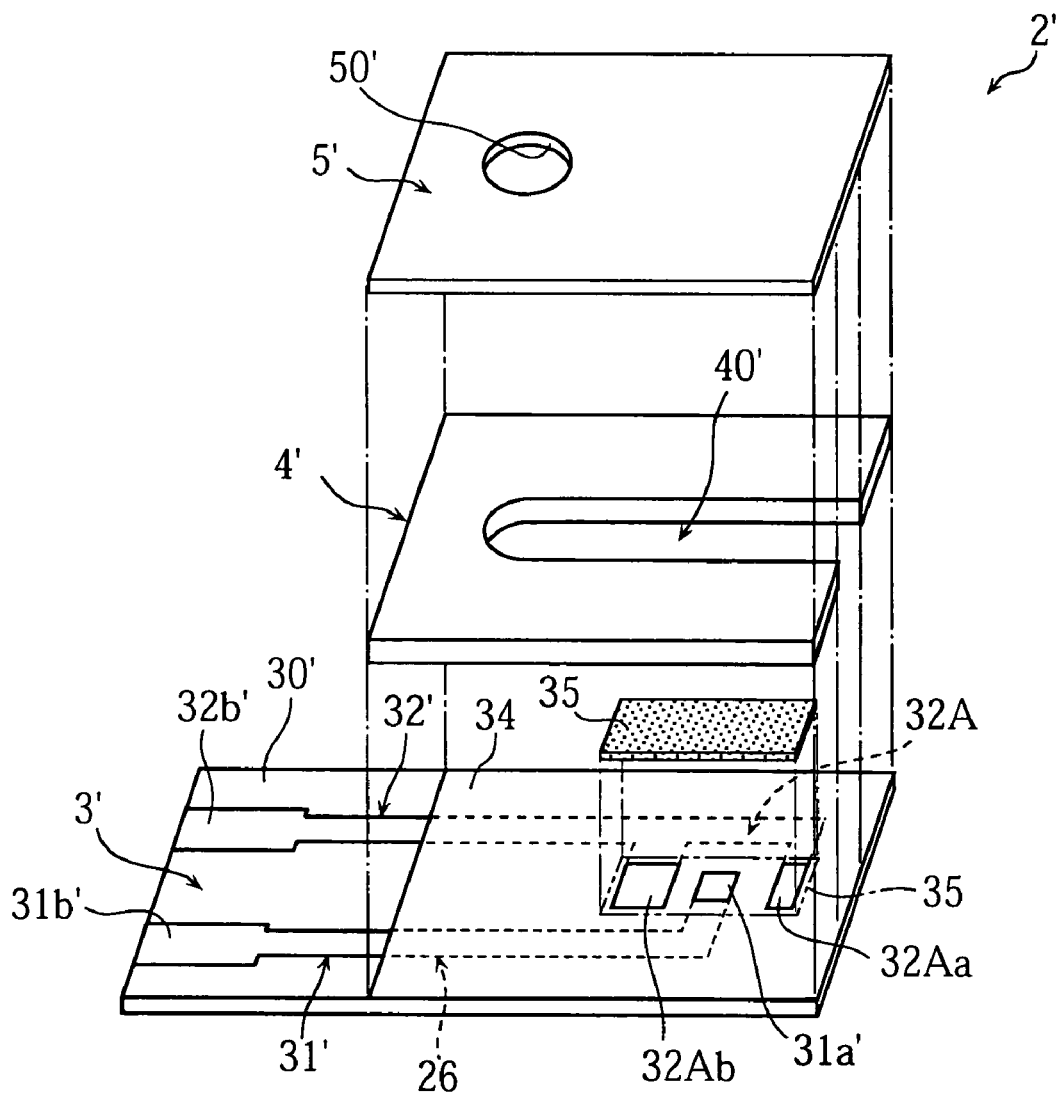
FIG. 8 is an exploded perspective view of the biosensor shown in FIG. 7.

As shown in FIGS. 7 and 8, the biosensor 2' includes a substrate 3', a spacer 4' and a cover 5', and a capillary 6' defined by these parts.

The substrate 3' has an upper surface 30' formed with an operative electrode 31' and a counterpart electrode 32'. Most part of the operative electrode 31' extends longitudinally of the substrate 3', but an end 31a' thereof extends widthwise of the substrate 3'. Most part of the counterpart electrode 32' extends longitudinally of the substrate 3'. The counterpart electrode 32' has an end 32A provided with a first extension 32Aa and a second extensions 32Ab which extend widthwise of the substrate. The second extension 32Ab is larger in surface area than the first extension 32Aa. Alternatively, the first extension 32Aa and the second extension 32Ab may be made generally equal to each other in surface area.

The end 31a' of the operative electrode 31' is located between the first extension 32Aa and the second extension 32Ab. The first extension 32Aa, the end 31a' and the second extension 32Ab are spaced from each other longitudinally of the substrate 3. A reagent portion 35 is provided on the portions 31a', 32Aa and 32Ab to connect these portions to each other.

The spacer 4' serves to define the height of the capillary 6'. The spacer 4' is formed with a slit 40' having an open end. The slit 40' defines the width of the capillary 6', and the open end of the slit 40' constitutes an introduction port 60' for introducing the sample liquid into the capillary 6'.

The cover 5' is formed with a discharge port 50'. The discharge port 50' communicates with the inside of the capillary 6' and serves to discharge air from the inside of the capillary 6' to the outside.

Figure 6:
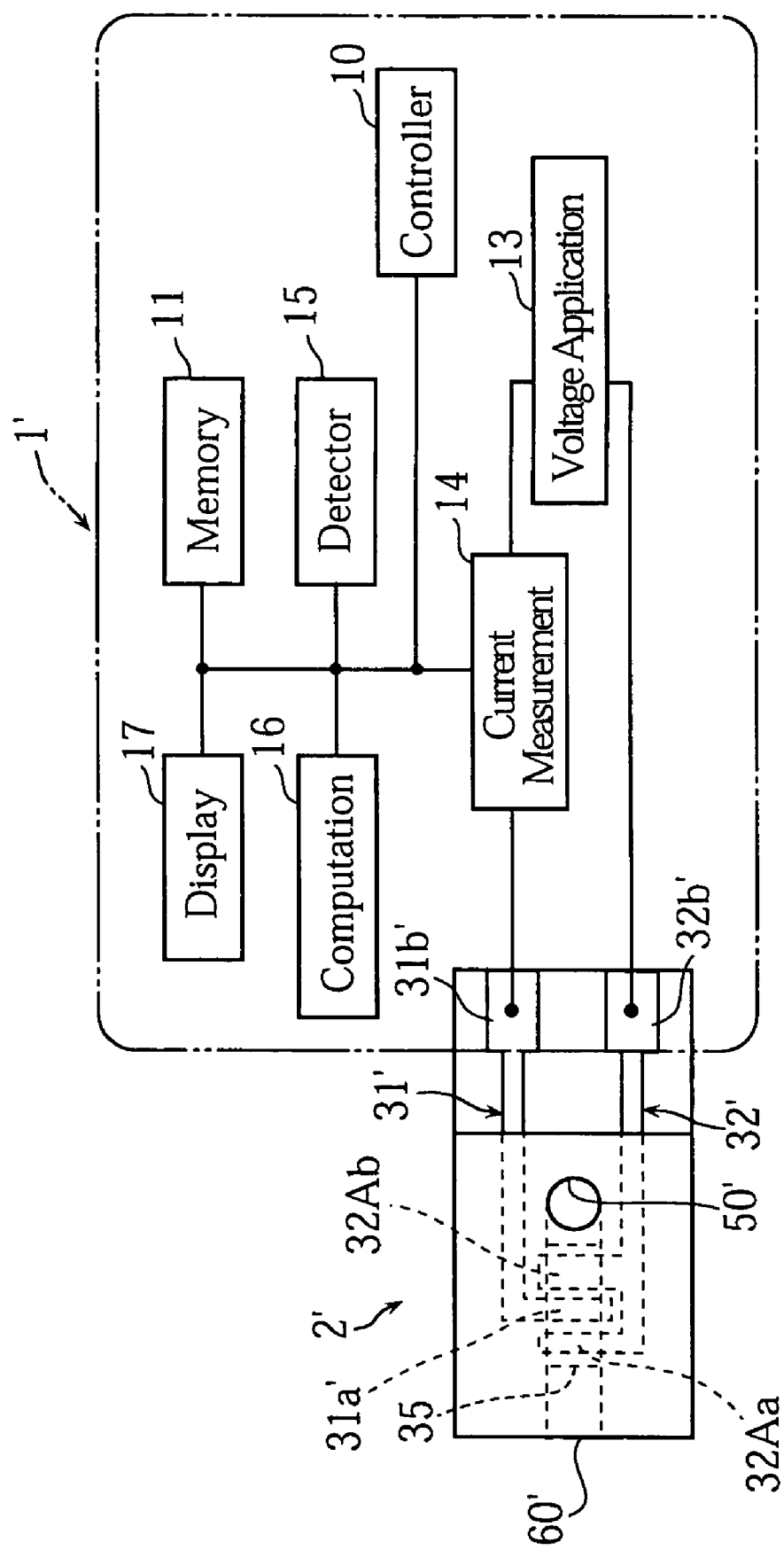
FIG. 6 is a view for describing a second embodiment of the present invention and schematically illustrates a concentration measuring apparatus to which a biosensor is attached.

Similarly to the concentration measuring apparatus 1 according to the first embodiment shown in FIG. 1, the concentration measuring apparatus 1' shown in FIG. 6 includes a controller 10, a memory 11, a voltage application unit 13, a current measurer 14, a detector 15, a computation unit 16 and a display 17. However, the concentration measuring apparatus 1' shown in FIG. 6 is not provided with a switching unit, because only the single counterpart electrode 32' is provided in the biosensor 2', as shown in FIGS. 7 and 8. Part of the programs and data stored in the memory 11 of the concentration measuring apparatus 1' differs from those of the concentration measuring apparatus 1 (See FIG. 1).

Figure 9:
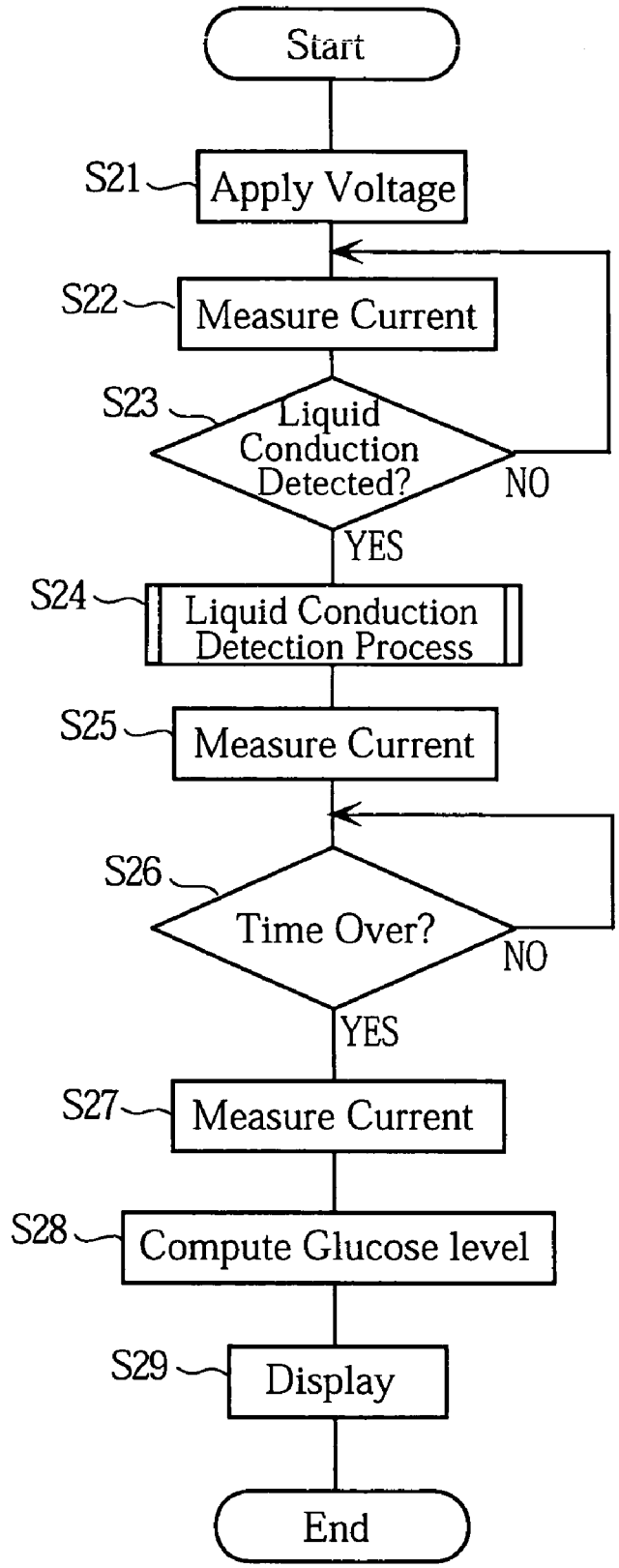
FIG. 9 is a flowchart for describing the concentration measurement operation.
Figure 10:
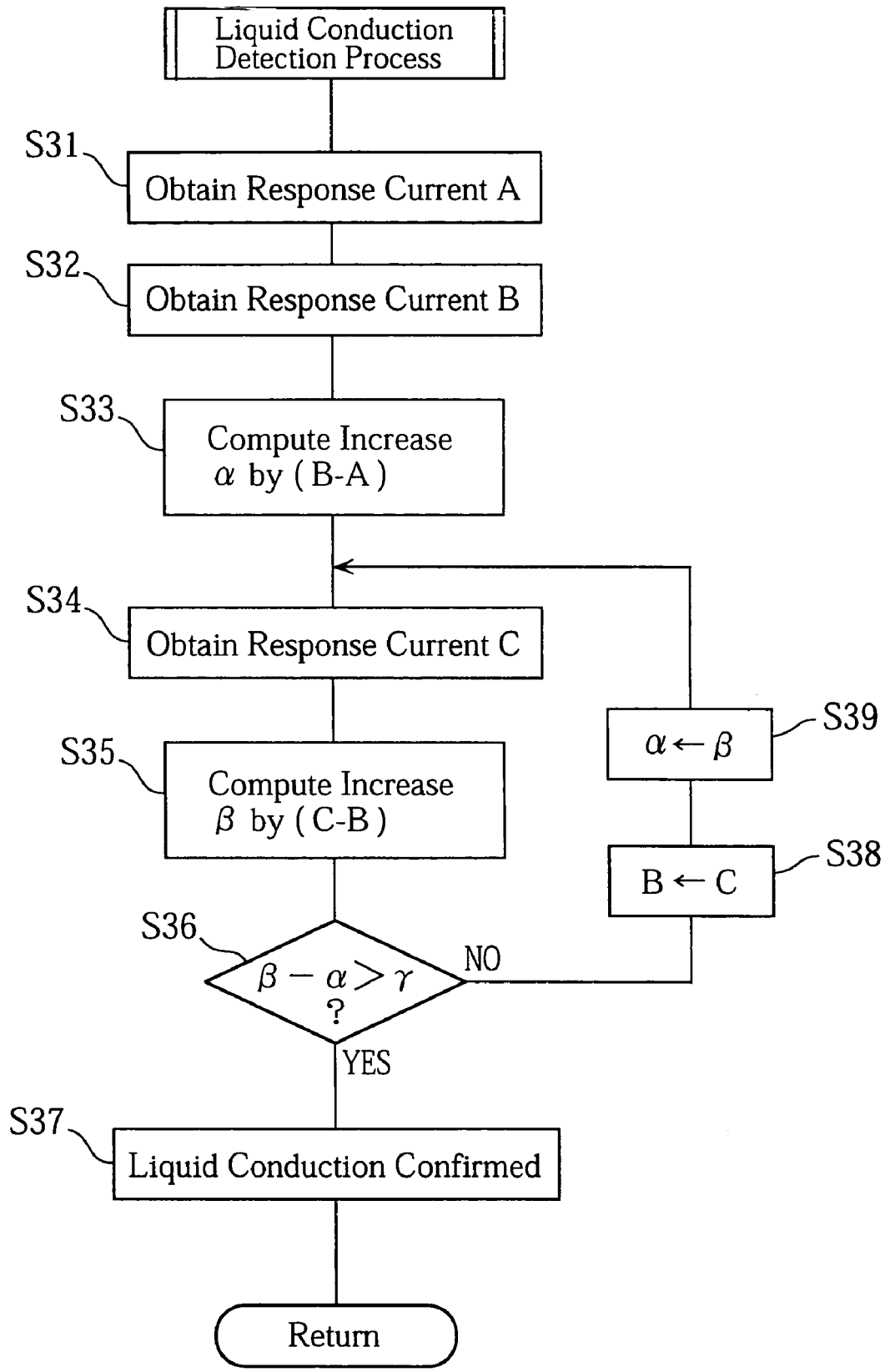
FIG. 10 is a flowchart for describing the liquid conduction detection process in the concentration measurement operation.
Figure 11:
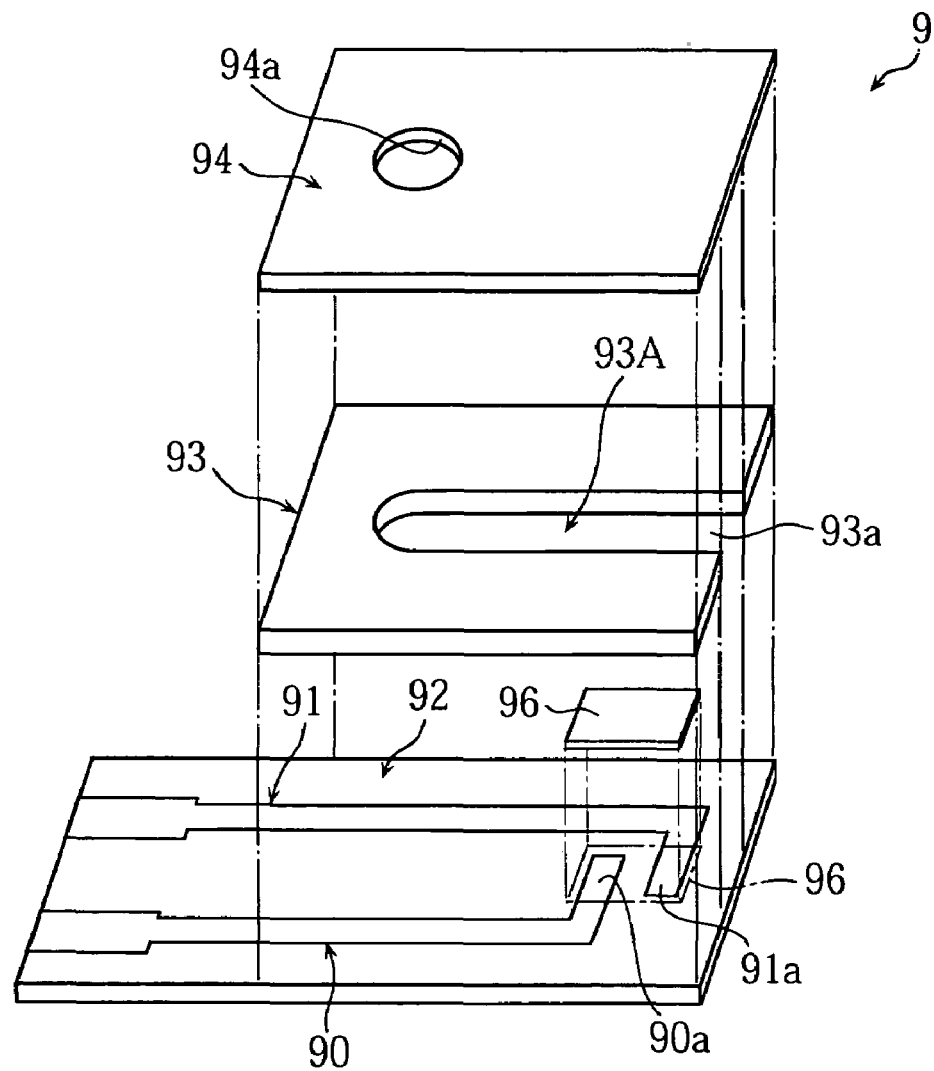
FIG. 11 is an exploded perspective view illustrating an example of prior art biosensor.
Figure 12:
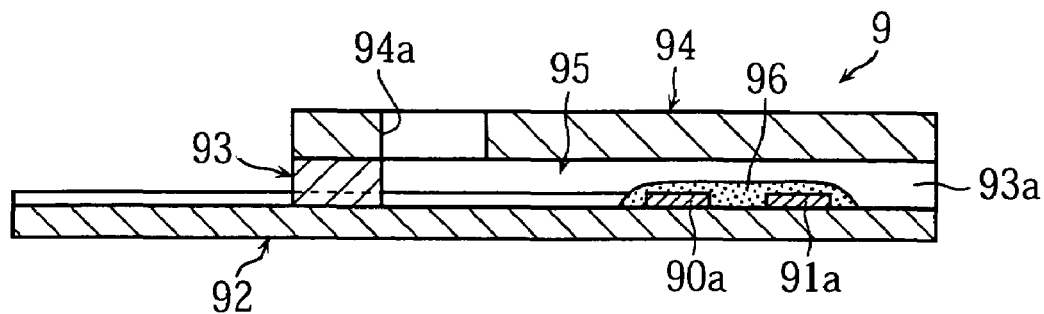
FIG. 12 is a sectional view of the biosensor shown in FIG. 11.

The method for measuring the blood glucose level using the concentration measuring apparatus 1' and biosensor 2' will be described below with reference to FIGS. 6-8 and the flowcharts shown in FIGS. 9 and 10.

First, for measuring the blood glucose level, the biosensor 2' is mounted to the concentration measuring apparatus 1', and blood is introduced into the capillary 6' of the biosensor 2' through the introduction port 60'.

In the concentration measuring apparatus 1', the voltage application unit 13 applies a voltage across the operative electrode 31' and the counterpart electrode 32' of the biosensor 2' (S21). The current measurer 14 measures a response current (S22). Based on the response current, it is determined whether or not liquid conduction is established between the end 31a' of the operative electrode 31' and the first extension 32Aa of the counterpart electrode 32' (S23). Specifically, the detector 15 monitors the response current measured by the current measurer 12 and checks whether or not the response current exceeds a predetermined threshold value. When the response current exceeds the threshold value, the detector 15 determines that liquid conduction is established between the end 31a' of the operative electrode 31' and the first extension 32Aa of the counterpart electrode 32' (S23: YES) When the response current does not exceed the threshold value, the detector determines that the liquid is not provided (S23: NO).

When the detector 15 does not detect the liquid conduction (S23: NO), the current measurement in S22 and the check in S23 are repetitively performed until the detector 15 detects the liquid conduction (S23: YES). In this case, the measurement of response current in S22 is performed every 0.05 to 0.2 seconds, for example. When the liquid conduction is not detected even when the check is performed more than a predetermined number of times or even after a predetermined time has elapsed, the operation may be treated as an error.

When the liquid conduction is detected by the detector 15 (S23: YES), the detector 15 determines that the blood has entered the capillary 6' and checks whether or not liquid conduction is established between the end 31a' of the operative electrode 31' and the second extension 32Ab of the counterpart electrode 32' (S24). By the process step S24, it is determined whether or not a sufficient amount of blood needed for measurement is supplied to the interior of the capillary 6'. The liquid conduction detection process in S24 is performed following the flowchart shown in FIG. 10, for example.

Specifically, in the liquid conduction detection process, the current measurer 14 measures the response current at predetermined intervals. A response current value A is obtained in the first measurement (S31), and a response current value B is obtained in the next sampling (S32). Subsequently, the response current value A is subtracted from the response current value B to figure out the increase $\alpha$ (S33). Then, a response current value C is obtained in the next sampling (S34). The response current value B is subtracted from the response current value C to figure out the increase $\beta$ (S35). Then, whether or not the difference between the increase $\beta$ and the increase $\alpha$ is greater than a predetermined threshold value $\gamma$ is determined (S36). When the difference between the increase $\beta$ and the increase $\alpha$ is greater than the predetermined threshold value $\gamma$ (S36: YES), the detector 15 determines that the liquid conduction is established between the end 31a' of the operative electrode 31' and the second extension 32Ab of the counterpart electrode 32' (S37). When the difference between the increase $\beta$ and the increase $\alpha$ is smaller than the predetermined threshold value $\gamma$ (S36: NO), the detector 15 determines that the liquid conduction is not provided. In this case, the process steps S31-S36 are repeated while using the current value C (S38) as the value B, using the increase $\beta$ as the increase $\alpha$ (S39) and obtaining the next measurement value.

In the liquid phase reaction system formed in the capillary 6', oxidation-reduction reaction proceeds. As noted above, the second extension 32Ab of the biosensor 2' is larger in surface area than the first extension 32Aa. Therefore, when the blood reaches the second extension 32Ab, the response current value changes largely. Therefore, in the liquid conduction detection process of S24, the liquid conduction between the end 31a' of the operative electrode 31' and the second extension 32Ab of the counterpart electrode 32' can be easily and reliably detected from the sharp change in the response current.

The detector 15 obtains the response current value when the liquid conduction is confirmed in S24 (S37). The response current value is stored in the memory 11, for example. Subsequently, the detector 15 checks, in Step S26, whether or not a predetermined time has elapsed since the liquid conduction was confirmed in S24 (S37). This check is repetitively performed until the detector 15 determines that the predetermined time has elapsed (S26: YES). When the detector 15 determines that the predetermined time has elapsed (S26: YES), the current measurer 14 measures the response current for the concentration computation (S27). Alternatively, the response current may be measured at predetermined intervals after the liquid conduction is confirmed in S24 (S37). In this case, the response current at a certain time after the detection of liquid conduction in S24 may be sampled and used as the response current for computation. The obtaining of the response current for computation in S27 may be performed after a predetermined time has elapsed since the liquid conduction was detected in S23.

Subsequently, the computation unit 16 computes the blood glucose level (S28). Specifically, for example, the difference between the response current for computation measured in S27 and the response current measured in S25 is computed, and the blood glucose level is computed utilizing the difference and the calibration curve stored in the memory 11. The computation result is displayed at the display 17 (S29).

As noted above, in the prior art method, whether or not a sufficient amount of blood necessary for measurement is supplied to the capillary is determined by the comparison between a predetermined threshold value and a measured response current. In this embodiment, on the other hand, the liquid conduction between the end 31a' of the operative electrode 31' and the second extension 32Ab of the counterpart electrode 32' is detected based on the increase of the response current (S36). Specifically, unlike the prior art method, the liquid conduction is detected based on the relative comparison between response current values obtained by measurement, not based on the absolute comparison between a predetermined threshold value and a response current value. Therefore, even when the response current values are influenced by hematocrit, the detection of liquid conduction can be performed accurately without being influenced by hematocrit. Accordingly, whether or not a sufficient amount of blood necessary for measurement is supplied to the capillary 6' can be detected reliably.

In this embodiment, the computation of the blood glucose level in S28 is performed based on the difference between the response current measured in S27 and the response current measured in S25. Since this difference is also a value obtained by relative comparison, the computation provides proper concentration value which is free from the influence of hematocrit.

In this embodiment, the correction similar to that of the first embodiment may be performed. Specifically, the time taken from the detection of liquid conduction between the end 31a' of the operative electrode 31' and the first extension 32Aa of the counterpart electrode 32' in S23 to the confirmation of liquid conduction between the end 31a' of the operative electrode 31' and the second extension 32Ab of the counterpart electrode 32' in S24 (S37) may be computed, and correction may be performed based on the time taken.

The present invention is not limited to the first embodiment and the second embodiment described above. For example, the invention is applicable to a sample liquid other than blood, e.g. urine. Further, the method of the present invention is applicable for measuring a component other than glucose, e.g. cholesterol. Instead of hematocrit, the amount of chyle or the degree of hemolysis of the sample liquid may be taken into consideration as a factor which influences the response current in the concentration measurement of the present invention.

The invention claimed is:

1. A concentration measuring method for measuring concentration of a particular component in a sample liquid using a test tool;

the test tool comprising: a capillary for moving the sample liquid, an operative electrode, a first counterpart electrode arranged upstream from the operative electrode in a moving direction of the sample liquid, a second counterpart electrode arranged downstream from the operative electrode in the moving direction of the sample liquid;

wherein the method comprises:

a first detection step for detecting whether or not liquid conduction is established between the operative electrode and the first counterpart electrode by detecting a response current between these two electrodes under voltage application;

a second detection step performed after conduction is detected in the first detection step for detecting whether or nor liquid conduction is established between the operative electrode and the second counterpart electrode by detecting the response current between these two electrodes for detecting a response current under voltage application;

a measurement step performed after conduction is detected in the second detection step for measuring a response current between the operative electrode and the first counterpart electrode or between the operative electrode and the second counterpart electrode under voltage application; and a concentration computation step for computing the concentration of the particular component based on the response current measured in the measurement step, the computation of the concentration being also based on a lapse time between conduction detection in the first detection step and conduction detection in the second detection step.

2. The concentration measuring method according to claim 1, wherein the concentration computation step includes data processing operation for correcting, based on a correction value, the response current measured in the measurement step or a computed value obtained based on the measured response current; and wherein the correction value is obtained by computation based on data showing a relationship between the lapse time and the correction value.

3. The concentration measuring method according to claim 1, wherein the sample liquid contains a coexisting component which causes an error in the concentration measurement of the particular component; and wherein the lapse is figured out as a reflection of influence of the coexisting component.

4. The concentration measuring method according to claim 3, wherein the sample liquid is blood containing blood cell components as the coexisting component.

5. The concentration measuring method according to claim 3, wherein the particular component is glucose.

6. A concentration measuring apparatus for measuring concentration of a particular component in a sample liquid using a test tool;

the test tool comprising: a capillary for moving the sample liquid, an operative electrode, a first counterpart electrode arranged upstream from the operative electrode in a moving direction of the sample liquid, a second counterpart electrode arranged downstream from the operative electrode in the moving direction of the sample liquid;

wherein the apparatus comprises:

a voltage application unit for applying a voltage between the operative electrode and the first counterpart electrode as well as between the operative electrode and the second counterpart electrode;

a current measurer for measuring a response current between the operative electrode and the first counterpart electrode under voltage application, the current measurer also measuring a response current between the operative electrode and the second counterpart electrode under voltage application;

a detector for detecting whether or not liquid conduction is established between the operative electrode and the first counterpart electrode by detecting the response current between these two electrodes under voltage application, the detector also detecting whether or not liquid conduction is established between the operative electrode and the second counterpart electrode by detecting the response current between these two electrodes under voltage application after conduction is detected between the operative electrode and the first counterpart electrode; and a computation unit for computing the concentration of the particular component based on a response current measured under voltage application between the operative electrode and the first counterpart electrode or between the operative electrode and the second counterpart electrode after conduction is detected between the operative electrode and the second counterpart electrode, the concentration computation being also based on a lapse time from conduction detection between the operative electrode and the first counterpart electrode to conduction detection between the operative electrode and the second counterpart electrode.

* * * * *